(12) United States Patent
Chiou et al.

(10) Patent No.: US 10,064,796 B2
(45) Date of Patent: Sep. 4, 2018

(54) SKIN TIGHTENING COMPOSITIONS

(71) Applicant: L'OREAL, Paris (FR)

(72) Inventors: Catherine Chiou, Saddle Brook, NJ (US); Angelike A. Galdi, Westfield, NJ (US)

(*) Notice: Subject to any disclaimer, the term of this patent is extended or adjusted under 35 U.S.C. 154(b) by 10 days.

(21) Appl. No.: 15/384,957

(22) Filed: Dec. 20, 2016

(65) Prior Publication Data

US 2017/0189288 A1 Jul. 6, 2017

Related U.S. Application Data

(63) Continuation of application No. 14/985,582, filed on Dec. 31, 2015.

(51) Int. Cl.
| | |
|---|---|
| A61K 33/00 | (2006.01) |
| A61K 8/25 | (2006.01) |
| A61K 8/34 | (2006.01) |
| A61K 8/73 | (2006.01) |
| A61K 8/81 | (2006.01) |
| A61K 8/86 | (2006.01) |
| A61K 8/87 | (2006.01) |
| A61K 8/891 | (2006.01) |
| A61K 8/892 | (2006.01) |
| A61K 8/895 | (2006.01) |
| A61Q 19/00 | (2006.01) |
| A61Q 19/08 | (2006.01) |
| A61K 8/26 | (2006.01) |

(52) U.S. Cl.
CPC .................. *A61K 8/25* (2013.01); *A61K 8/26* (2013.01); *A61K 8/345* (2013.01); *A61K 8/73* (2013.01); *A61K 8/8147* (2013.01); *A61K 8/8152* (2013.01); *A61K 8/8164* (2013.01); *A61K 8/8176* (2013.01); *A61K 8/86* (2013.01); *A61K 8/87* (2013.01); *A61K 8/891* (2013.01); *A61K 8/892* (2013.01); *A61K 8/895* (2013.01); *A61Q 19/00* (2013.01); *A61Q 19/007* (2013.01); *A61Q 19/08* (2013.01); *A61K 2800/48* (2013.01); *A61K 2800/548* (2013.01); *A61K 2800/596* (2013.01)

(58) Field of Classification Search
CPC .. A61K 8/8152; A61K 8/8164; A61K 8/8176; A61K 8/86; A61K 8/87; A61K 8/891; A61K 8/892; A61K 8/895; A61Q 19/00; A61Q 19/007; A61Q 19/08
See application file for complete search history.

(56) References Cited

U.S. PATENT DOCUMENTS

| | | | |
|---|---|---|---|
| 5,370,876 A * | 12/1994 | Noll | A01N 25/24 424/407 |
| 2013/0189332 A1 | 7/2013 | Breyfogle et al. | |
| 2013/0195783 A1 * | 8/2013 | Breyfogle | A61K 8/25 424/62 |
| 2015/0373380 A1 | 12/2015 | Tsukagoshi et al. | |
| 2017/0042783 A1 * | 2/2017 | Imoto | A61K 8/64 |

FOREIGN PATENT DOCUMENTS

EP   2404642 A2   1/2012

* cited by examiner

*Primary Examiner* — Nannette Holloman

(57) ABSTRACT

The present disclosure relates to cosmetic compositions that provide immediate skin-tightening and long-lasting improvements to the skin for the treatment of, for example, eye bags, facial wrinkles, and other age-related skin imperfections. The compositions comprise: (a) a first film former potassium silicate; (b) at least one second film former; (c) at least one polyvalent silicate thickener; (d) at least one anionic associative polymeric thickener; (e) at least one plasticizer; and (f) optionally at least one cosmetic powder.

20 Claims, No Drawings

SKIN TIGHTENING COMPOSITIONS

CROSS-REFERENCE TO RELATED APPLICATIONS

This patent application claims benefit of U.S. patent application Ser. No. 14/985,582, filed on Dec. 31, 2015, entitled "SKIN TIGHTENING COMPOSITION," the disclosure of which is incorporated by reference as if fully rewritten herein.

FIELD OF THE DISCLOSURE

The present disclosure relates to cosmetic compositions that provide immediate and long-lasting improvement to the skin. In particular, the compositions provide a physical tightening effect to the skin and are therefore useful for treating eye bags, facial wrinkles, and other age-related skin imperfections.

BACKGROUND OF THE DISCLOSURE

Skin produces less collagen and elastin as it ages. For example, after the age of twenty, a person (human) produces about 1 percent less collagen in the skin each year. As a result, the skin becomes thinner and more fragile. Inevitably, wrinkles, crow's feet, age-spots, eye bags, and the like, begin to form.

Consumers often wish to improve the appearance of such age-related skin imperfections, preferably with instantaneous results. Many consumer products and procedures devoted to hiding and reducing wrinkles are available. Some products and procedures are simple and inexpensive, for example, applying make-up, particularly a primer or colored foundation, to cover the skin (and thereby cover and/or fill the wrinkles and provide a smoother look). Far more expensive and drastic procedures, such as surgical face lifts and Botox® injections, are also used to reduce the appearance of wrinkles. However, many consumers either cannot afford, or do not wish, to undergo such drastic cosmetic procedures. There are a number of lotions and creams which are formulated to hydrate the skin and make it more supple, thereby reducing the appearance of wrinkles. Some of these products contain active ingredients, for example, niacinamide, that help repair and rejuvenate skin over time. Unfortunately, however, all of these products and procedures have drawbacks.

Make-up products are often visible, offer minimal texture benefits, and have no long-term lasting effect on the skin. After removal of the make-up, the skin looks the same as before the make-up was applied. Common skin care products can have chronic, acute or both effects on the skin. Hydration and optical effects are common acute benefits, but these benefits quickly wear-off over time.

Attempts have been made to develop new categories of products to improve the appearance of skin without the drawbacks of existing products and procedures. One such family of products can be generally classified as "adhesive, contractile film formers". Film formers are chemical compositions that when applied to skin, leave a pliable, cohesive and continuous covering. A select group of film formers are also adhesive to the skin and contractile.

The instant disclosure is directed to new and improved long-lasting skin tightening compositions that do not suffer the drawbacks of other skin-tightening compositions.

BRIEF SUMMARY OF THE DISCLOSURE

The current disclosure relates to a skin tightening composition that imparts an instant sensation and physical skin tightening effect upon application to the skin, in particular, to eye bags and eye or facial wrinkles, without the drawbacks of other products. The present disclosure relates to a skin tightening film forming composition, which is typically an aqueous composition, comprising:
 (a) a first film former potassium silicate;
 (b) at least one second film former;
 (c) at least one polyvalent silicate thickener;
 (d) at least one anionic associative polymeric thickener;
 (e) at least one plasticizer; and
 (f) optionally, at least one cosmetic powder.

The composition typically provides an immediate tightening of the skin and smooths imperfections of the skin upon application.

The composition may have an alkaline pH, for example, it may have a pH value from about to 10 to about 12. Furthermore, the composition may be in the form of a liquid dispersion, a gel, a cream, a lotion, a mousse, or a spray. Likewise, the composition may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form.

The instant disclosure also relates to methods for improving the appearance of skin comprising applying the compositions described herein to the skin. For example, the instant disclosure relates to methods for firming and/or tightening the skin comprising applying the compositions described herein to the skin and forming a skin-tightening film or layer on the skin. In some instances, the compositions are applied to the skin of the face, and/or more specifically around the eyes, around the mouth, and/or around the neck of a human face. The methods of improving the appearance of skin include methods for treating or reducing the appearance of wrinkles, blemishes, dryness, roughness, dullness, age spots, sagging, and/or puffy skin.

The compositions of the present disclosure are surprisingly stable, elastic, and provide an unexpectedly long-lasting skin tightening effect to the skin. Unlike other products, the films formed on the skin with the instant compositions do not dry-out and whiten, crack, or peel. Instead, they remain flexible (elastic), durable, and comfortable. Moreover, the compositions (and resulting films) hydrate and protect the underlying skin.

DETAILED DESCRIPTION OF THE DISCLOSURE

As mentioned previously, the present disclosure relates to cosmetic compositions that provide instantaneous and long-lasting improvement to the skin. In particular, the compositions provide a tightening effect on skin and are therefore useful for treating eye bags, facial wrinkles, and other age-related skin imperfections. Typically, the compositions of the instant disclosure comprise: (a) a first film former potassium silicate; (b) at lease one second film former; (c) at lease one polyvalent silicate thickener; (d) at least one anionic associative polymeric thickener; (e) at lease one plasticizer; and (f) optionally, at least one cosmetic powder. For example, the compositions may comprise:
 (a) from about 1% to about 10% by weight of first film former potassium silicate;
 (b) from about 0.1% to about 10% by weight of at least one second film former;
 (c) from about 0.3% to about 2% by weight of at least one polyvalent silicate thickener;

(d) from about 0.5% to about 10% by weight of at least one anionic associative polymeric thickener;
(e) from about 2% to about 18% by weight of at least one plasticizer; and
(f) optionally, from about 0.1% to about 10% by weight of at least one cosmetic powder.

Upon application to the skin, the compositions provide an immediate tightening sensation and reduce skin imperfections.

The compositions can have an alkaline pH. For example, in some cases, the pH may be in the range of 10 to 12, 10.5 to 11.5, or 11 to 11.5.

The cosmetic composition described herein contains potassium silicate. Potassium silicate is an inorganic compound. The most common formula is K2SiO3 and it contains various quantity of water. Potassium silicates are well known to those skills in the art and are commercially available from PQ® Potassium Silicates. It is used as a film former.

Typically, the film former potassium silicate is present in an amount from 1% to 10%, 2% to 9%, 3% to 8%, 3% to 7%, 4% to 6%, or 4% to 5%, by weight of the total weight of the composition.

The at least one second film former may be selected from the group consisting of colloidal silica, pullulan, Polycacrylate-21 (and) acrylates/dimethylaminoethylmethacrylate copolymer, Polyurethanes, polysaccharides, polyvinylpyrrolidone, polyacrylates, acrylates copolymer, and mixtures thereof. In some cases, the second film former is a polysaccharide, which may have one or more free hydroxyl groups. Furthermore, in some cases, the polysaccharide is pullulan. Typically, the second film former is present in an amount from 0.1% to 10%, 1% to 8%, 2% to 7%, or 3% to 6%, by weight of the total composition.

The total amount of the film former potassium silicate and the additional film former(s) (i.e., the total weight of all film formers in the composition) may be present in an amount from 1% to 20%, 1% to 18%, 1% to 16%, 1% to 14%, 1% to 12%, 1% to 10%, 1% to 8%, 2% to 20%, 2%, 18%, 2% to 16%, 2% to 16%, 2% to 14%, 2% to 12%, 2% to 10%, 2% to 8%, 3% to 20%, 30% to 18%, 30% to 16%, 3% to 14%, 3% to 12%, 3% to 10%, 3% to 8%, 4% to 20%, 4% to 18%, 4% to 16%, 4% to 14%, 4% to 14%, 4% to 12%, 4% to 10%, 4% to 8%, 5% to 20%, 5% to 18%, 5% to 16%, 5% to 14%, 5% to 12%, 5% to 10%, 5% to 8%, or 3% to 15%, by weight of the total weight of the composition.

The polyvalent silicate thickener may be selected from the group consisting of magnesium silicate, calcium silicate, aluminum silicate, a polyvalent silicate clay, montmorillonite, bentonite, smectite, and mixtures thereof. In some cases, the polyvalent silicate thickener is montmorillonite. In some cases, the polyvalent silicate thickener is organically modified clay such as kaolinite, smectite, bentonite, and/or montmorillonite The polyvalent silicate thickener is typically present in an amount of 0.1% to 2%, 0.1% to 1.5%; 0.1% to 1%, 0.1% to 0.9%, 0.1% to 0.8%, 0.1% to 0.7%, 0.2% to 2%; 0.2% to 1.5%, 0.2% to 1%, 0.2% to 0.9%, 0.2% to 0.8%, 0.2% to 0.7%, 0.3% to 2%, 0.3% to 1.5%, 0.3% to 1%, 0.3% to 0.9%, 0.3% to 0.8%, 0.3% to 0.7%, 0.4% to 2%, 0.4% to 1.5%, 0.4% to 1%, 0.4% to 0.9% %, 0.4% to 0.8%, 0.4% to 0.7%, 0.4% to 0.6%, or about 0.5%.

The compositions of the disclosure typically include at least one anionic associative polymeric thickener. The at least one anionic associative polymeric thickener may be selected from the group consisting of an acrylate copolymer, an acrylates/beheneth-25 methacrylate copolymer, an acrylates/steareth-20 methacrylate copolymer, and mixtures thereof. Furthermore, the at least one anionic associative polymeric thickener may include acrylates/steareth-20 methacrylate copolymer such as Aculyn™ 22 (Dow Chemical Company); acrylates/beneneth-25 methacrylate copolymer such as Novethix™ (Lubrizol); acrylate copolymer such as Carbopol® Aqua SF-1 Polymer (Lubrizol). The at least one anionic associative polymer thickener is typically present in an amount from 0.5% to 15%, 1% to 15%, 1% to 14%, 1% to 13%, 1% to 12%, 1% to 10%, 1% to 8%, 2% to 15%, 2% to 14%, 2% to 13%, 2% to 12%, 2% to 10%, 2% to 8%, or 2% to 6%, by weight of the total composition. Many anionic associative polymeric thickeners are water-soluble, and increase the viscosity of water or form an aqueous gel when the cosmetic compositions of the disclosure are dispersed/dissolved in water.

The compositions of the disclosure typically include at least one plasticizer. The at least one plasticizer may be, for example, propylene glycol, polyethylene glycol, glycerol, sorbitol, dipropylene glycol, glycerin, propane diol, triethyl citrate, isohexadecane, and sodium hyaluronate. Typically, the plasticizer is present in an amount of 1% to 18%, 1% to 16%, 1% to 14%, 1% to 13%, 1% to 12%, 1% to 11%, 1%, to 10%, 2% to 18%, 2% to 16%, 2% to 14%, 2% to 13%, 2% to 12%, 2% to 11%, 2% to 10%, 5% to 18%, 5% to 16%, 5% to 14%, 5% to 13%, 5% to 12%, 5% to 11%, 5% to 10%, or 9% to 11% by weight of the total weight of the composition.

The compositions described herein may include at least one cosmetic powder. Cosmetic powders can be used to help formulate compositions that are smooth and soft on the skin. Representative cosmetic powders include, but are not limited to, talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders, such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder, such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder, such as hydroxyethyl cellulose and sodium carboxymethyl cellulose, ethylene glycol monostearate; inorganic white pigments, such as magnesium oxide. Representative cosmetic powders include, for example, polymethylsilsesquioxane, methyl polymethacrylate crosspolymer, Nylon-12, silica and boron nitride, and combinations thereof.

In some cases, the cosmetic powder may be selected from the group consisting of talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polymethyl Methacrylate, polystyrene powder, silk powder, crystalline cellulose, and mixtures thereof. In some cases, the cosmetic powder is polymethyl methalcrylate.

When present, the one or more cosmetic powders may be present in an amount of 0.1% to about 25%, 0.1% to 20%, 0.1% to 15%, 0.1% to 10%, 0.1% to 8%, 0.1% to 6%, 0.1% to 4%, 0.5% to 20%, 0.0.5% to 15%, 0.5% to 10%, 0.5% to 8%, 0.5% to 6%, 0.5% to 4%, 1% to 20%, 1% to 15%, 1% to 10%, 1% to 8%, 1% to 6%, 1% to 4%, 2% to 10%, 2% to 8%, 2% to 6%, or 3% to 7%, based on the total weight of the composition.

The instant disclosure also relates to methods for improving the appearance of skin comprising applying the compositions described herein to the skin. Furthermore, the instant disclosure relates to methods for firming and/or tightening the skin comprising applying the compositions described herein to the skin and forming a skin-tightening film or layer on the skin. In some instances, the compositions are applied to the skin of the face, and/or more specifically around the eyes, around the mouth, and/or around the neck. The methods of improving the appearance of skin include methods for treating or reducing the appearance of wrinkles, blemishes, dryness, roughness, dullness, age spots, sagging, and/or puffy skin.

The compositions of the present disclosure may be in the form of a liquid dispersion, a gel, a cream, a lotion, a mousse, or a spray. The composition may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form.

The compositions of the present disclosure are typically aqueous compositions. For example, the compositions may have 20% to 80%, 20% to 70%, 20% to 60%, 20% to 50%, 20% to 40%, 20% to 30%, 30% to 80%, 30% to 70%, 30% to 60%, 30% to 50%, 30% to 40%, 35% to 65%, or 40% to 60% water.

EXAMPLES

The following Examples are provided for illustrative purposes only, and are not intended to be limiting.

Example 1

TABLE 1

| Ingredient/US INCI Name | Formula | | |
|---|---|---|---|
| | Ex. 1 % | Ex. 2 % | Ex. 3 % |
| Potassium Silicate | 3.5-5.0 | 5.5-5.8 | 6-6.8 |
| Polyvalent Silicate[1] | 0.80-1.0 | 0.5-0.7 | 0.4-0.6 |
| Acrylates Copolymer | 7-10 | 6-10 | 11-15 |
| Second Film Former[2] | 4.0-5.0 | 4.0-5.0 | 0.2-0.5 |
| Methyl Methacrylate Crosspolymer (and) Mineral Oil | 0.0-0.1 | 2.5-3.0 | 2.5-3.0 |
| Cosmetic Powder | 3.0 | 3.0 | 3.0 |
| Water | QS | QS | QS |
| Plasticizer[3] | 3.0-6.0 | 8.0-10.0 | 13-15 |

[1]Vermiculite, Montmorillonite, Smectite.
[2]Polyurethanes, Polysaccharides (Pullulan), Polyvinylpyrrolidone, Acrylates and Colloidal Silicate.
[3]Propylene Glycol, Polyethylene Glycol, Glycerol, Sorbitol, Dipropylene Glycol, Glycerin, Propanediol, Triethyl Citrate, Isohexadecane

TABLE 2

| Ingredient/US INCI Name | Formula | | | | | |
|---|---|---|---|---|---|---|
| | Ex. 4 % | Ex. 5 % | Ex. 6 % | Ex. 7 % | Ex. 8 % | Ex. 9 % |
| Potassium Silicate | 5 | 3 | 5 | 5 | 5 | 5 |
| Citric Acid | 0 | 0 | 1 | 0 | 1 | 1 |
| Glycerin | 5 | 7 | 3 | 3 | 0 | 7 |
| Gum | 0 | 0 | 0.6 | 0.4 | 0.4 | 0.4 |
| Magnesium Aluminum Silicate (Smectite) | 0 | 0 | 2 | 2 | 2 | 1.5 |
| Sodium Stearoyl Glutamate | 0 | 0 | 0 | 0 | 0.75 | 0 |
| Cetearyl Ethylhexanoate (and) Isopropyl Myristate (90/10) | 0 | 0 | 0 | 0 | 4 | 4 |
| Dimethicone | 17.5 | 17.5 | 3 | 3 | 0 | |
| Dimethicone (5 cst) | 0 | 0 | 3 | 3 | 3 | 3 |
| Dimethicone (and) Dimthiconol | 0 | 0 | 1 | 1 | 1 | 1 |
| Dimethicone (and) Dimethicone/vinyl Dimethicone Crosspolymer (76/24) | 17 | 17 | 0 | 0 | 0 | 0 |
| Isononyl Isononanoate | 5 | 5 | 0 | 0 | 0 | 0 |
| Silica Silylate | 0.8 | 0 | 0 | 0 | 0 | 0 |
| Magnesium Sulfate | 0 | 0.5 | 0 | 0 | 0 | 0 |
| Sodium Citrate | 0.2 | 0 | 0 | 0 | 0 | 0 |
| Sodium Chloride | 0.5 | 0 | 0 | 0 | 0 | 0 |
| Boron Nitride | 1 | 0 | 0 | 0 | 0 | 0 |
| Vinyl Dimethicone/Methicone Sisesquioxane | 5 | 5 | 0 | 0 | 0 | 0 |
| Polysorbate 20 | 0 | 0 | 0.5 | 0.5 | 0.5 | 0.5 |
| Carbomer | 0 | 0 | 0 | 0.4 | 0 | 0 |
| Water | QS | QS | QS | QS | QS | QS |

In making the formulations in the above tables, the following procedure may be used. The polyvalent silicate is introduced in portions with medium sweep and shear to the main kettle containing water at room temperature and mixed for about 5 to 10 minutes, or until the ingredient is fully hydrated and the mixture is homogenous. The polysaccharide is added in portions with medium sweep and shear. Then, the cosmetic powder is added. The mixture is mixed for 5 to 10 minutes or until uniform. The plasticizer is added and mixed for 5 minutes or until uniform. The homogenizer is turned off. Then, the vacuum is pulled until air bubbles are removed. The anionic associative polymeric thickener is slowly added directly to the main kettle as to not cause aeration. While still under the vacuum, continue to mix the ingredients. The potassium silicate is added slowly to neutralize the thickener, using low sweep and pull vacuum. Mixing is continued until the thickener is neutralized and the formula appears uniform.

pH Study with Composition Containing Potassium Silicate

A study of the pH was performed. The results showed that if the pH is below 10, the composition became more solid. However, it was found that when the pH is in the range of 10 to 12, or 11 to 11.5, the composition exhibits special properties. For example, the composition exhibited excellent film-forming properties on the skin and the film exhibited unexpectedly long-lasting strength, durability, and flexibility (elasticity).

As used herein, all percentages are by weight (wt. %) of the total composition.

All numeric ranges are inclusive of narrower ranges; delineated upper and lower range limits are interchangeable to create further ranges not explicitly delineated. All ranges and values disclosed herein are inclusive and combinable. For examples, any value or point described herein that falls within a range described herein can serve as a minimum or maximum value to derive a sub-range, etc.

As used herein, the term "tightening" means that the film contracts in a manner that skin has a tighter sensation to the user, and smooths skin imperfections upon application on the skin, which reduces the visual appearance of wrinkles in the skin.

As used herein, the terms "comprising," "having," and "including" are used in their open, non-limiting sense.

The terms "a," "an," and "the" are understood to encompass the plural as well as the singular.

The expression "at least one" means "one or more" (and vice versa) and thus includes individual components as well as mixtures/combinations.

"Film former" or "film forming agent" as used herein means a polymer or resin that leaves a film on the substrate to which it is applied, for example, after a solvent accompanying the film former has evaporated, absorbed into and/or dissipated on the substrate.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The foregoing description illustrates and describes the disclosure. Additionally, the disclosure shows and describes only the exemplary embodiments but, as mentioned above, it is to be understood that it is capable to use in various other combinations, modifications, and environments and is capable of changes or modifications within the scope of the disclosed concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

The invention claimed is:

1. A skin tightening aqueous film forming composition comprising:
   (a) from about 5% to about 10% by weight of a first film former potassium silicate;
   (b) from about 0.1% to about 10% by weight of at least one second film former;
   (c) from about 0.3% to about 2% by weight of at least one polyvalent silicate thickener;
   (d) from about 0.5% to about 10% by weight of at least one anionic associative polymeric thickener;
   (e) from about 2% to about 18% by weight of at least one plasticizer selected from the group consisting of glycerin, propylene glycol, butylene glycol, and propanediol; and
   (f) optionally from about 0.1% to about 10% by weight of at least one cosmetic powder;
   wherein the composition provides a tightening sensation and reduces skin imperfections upon application to the skin.

2. The composition of claim 1, wherein the (a) first film former potassium silicate is present in an amount from about 3% to about 8% by weight of the total weight of the composition.

3. The composition of claim 1, wherein the (b) at least one second film former is selected from the group consisting of colloidal silica, pullulan, polycacrylate-21 (and) acrylates/dimethylaminoethylmethacrylate copolymer, polyurethanes, polysaccharides, polyvinylpyrrolidone, polyacrylates, acrylates copolymer, and mixtures thereof.

4. The composition of claim 3, wherein the (b) at least one second film former comprises a polysaccharide.

5. The composition of claim 4, wherein the polysaccharide is pullulan.

6. The composition of claim 4, wherein the polysaccharide contains one or more free hydroxyl groups.

7. The composition of claim 1, wherein the second film former(s) is/are present in an amount from about 0.1% to about 2.0% by weight of the total composition.

8. The composition of claim 1, wherein the (c) at least one polyvalent silicate thickener is selected from the group consisting of magnesium silicate, calcium silicate, aluminum silicate, a polyvalent silicate clay, montmorillonite, bentonite, magnesium aluminum silicate, smectite, and mixtures thereof.

9. The composition of claim 1, wherein the (c) at least one polyvalent silicate thickener comprises montmorillonite.

10. The composition of claim 1, wherein the polyvalent silicate thickener(s) is/are present in an amount of 0.4% to 0.6% by weight of the total composition.

11. The composition of claim 1, wherein the polyvalent silicate thickener(s) is/are present in an amount of about 0.5% by weight of the total composition.

12. The composition of claim 1, wherein the (d) at least one anionic associative polymeric thickener is selected from the group consisting of an acrylate copolymer, an acrylates/beheneth-25 methacrylate copolymer, an acrylates/steareth-20 methacrylate copolymer, and mixtures thereof.

13. The composition of claim 1, wherein the anionic associative polymeric thickener(s) is/are present in an amount from about 3% to about 6% by weight of the total composition.

14. The composition of claim 1, wherein the plasticizer(s) is/are present in an amount from about 3% to about 15% by weight of the total composition.

15. The composition of claim 1, wherein the composition comprises a (f) at least one cosmetic powder selected from the group consisting of talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polymethyl Methacrylate, polystyrene powder, silk powder, crystalline cellulose, and mixtures thereof.

16. The composition of claim 15, wherein the (f) at least one cosmetic powder comprises polymethyl methacrylate.

17. The composition of claim 1, wherein the pH of the composition is from about 10 to about 12.

18. A method for improving the appearance of skin comprising applying the composition of claim 1 to the skin.

19. The methods of claim 18, wherein improving the appearance of skin comprises treating or reducing the appearance of wrinkles, blemishes, dryness, roughness, dullness, age spots, sagging, eye bags, and/or puffy skin.

20. A method for firming and/or tightening the skin comprising applying the composition of claim 1 to the skin.

* * * * *